US011850423B2

(12) United States Patent
Jin et al.

(10) Patent No.: US 11,850,423 B2
(45) Date of Patent: Dec. 26, 2023

(54) ELECTROCHEMICAL DEVICE COMPRISING AN ACUPUNCTURE ELECTRODE AND ITS USE FOR TREATING CANCER

(71) Applicant: Changchun Institute of Applied Chemistry Chinese Academy of Sciences, Jilin (CN)

(72) Inventors: Yongdong Jin, Changchun (CN); Guohua Qi, Changchun (CN); Bo Wang, Changchun (CN)

(73) Assignee: CHANGCHUN INSTITUTE OF APPLIED CHEMISTRY CHINESE ACADEMY OF SCIENCES, Jilin (CN)

( * ) Notice: Subject to any disclaimer, the term of this patent is extended or adjusted under 35 U.S.C. 154(b) by 24 days.

(21) Appl. No.: 17/624,758

(22) PCT Filed: Sep. 4, 2019

(86) PCT No.: PCT/CN2019/104391
§ 371 (c)(1),
(2) Date: Jan. 4, 2022

(87) PCT Pub. No.: WO2021/042291
PCT Pub. Date: Mar. 11, 2021

(65) Prior Publication Data
US 2022/0257939 A1    Aug. 18, 2022

(51) Int. Cl.
*A61N 1/36*    (2006.01)
(52) U.S. Cl.
CPC .............................. *A61N 1/36002* (2017.08)

(58) Field of Classification Search
CPC .............. A61N 1/36002; A61N 1/0432; A61N 1/0436; A61N 1/306; A61N 1/0502; A61N 1/36017; A61N 5/0619; A61H 39/08
See application file for complete search history.

(56) References Cited

U.S. PATENT DOCUMENTS

| 7,526,334 | B2 | 4/2009 | Herbst et al. |
| 10,342,973 | B2 | 7/2019 | Avent et al. |

(Continued)

FOREIGN PATENT DOCUMENTS

| CN | 2057590 U | 5/1990 |
| CN | 2618622 Y | 6/2004 |

(Continued)

OTHER PUBLICATIONS

Yin, Rui, *The Advance in Electrochemical Treatment Processor of Cancer*, Biomedical Engineering Research Center of Beijing, University of Aeronautics and Astronautics, vol. 3, No. 2, Dec. 31, 1997, pp. 7-10.

(Continued)

*Primary Examiner* — Tammie K Marlen
(74) *Attorney, Agent, or Firm* — Alston & Bird LLP

(57) ABSTRACT

The invention discloses an electrochemical device for treating cancer, characterized by using an acupuncture needle as a working electrode to produce hydrogen in a tumor tissue, thereby destroying the tumor tissue through the produced hydrogen gas. The device of the invention has low cost and simple operation, can realize minimally invasive treatment, and is green and environmentally friendly.

14 Claims, 9 Drawing Sheets

(56) References Cited

U.S. PATENT DOCUMENTS

2004/0010290 A1* 1/2004 Schroeppel .............. A61N 1/30
607/3
2010/0298821 A1* 11/2010 Garbagnati ........ A61B 18/1477
606/33

FOREIGN PATENT DOCUMENTS

| CN | 200991509 Y | 12/2007 |
| --- | --- | --- |
| CN | 105555360 A | 5/2016 |
| CN | 108420723 A | 8/2018 |

OTHER PUBLICATIONS

International Search Report for PCT/CN2019/104391 (ISA/CN) with English translation dated May 28, 2020 (9 pages).
Written Opinion for PCT/CN2019/104391 (ISA/CN) dated May 28, 2020.

* cited by examiner

ELECTROCHEMICAL DEVICE COMPRISING AN ACUPUNCTURE ELECTRODE AND ITS USE FOR TREATING CANCER

CROSS-REFERENCE TO RELATED APPLICATIONS

This application is a national phase entry of International Application No. PCT/CN2019/104391, filed Sep. 4, 2019, the entire contents of which are incorporated herein by reference.

TECHNICAL FIELD

The invention belongs to the field of medical device, and relates to an electrochemical device comprising an acupuncture electrode and its use for treating cancer.

BACKGROUND

With the improvement of human living standards, people have a higher awareness of disease prevention and treatment. Cancer is one of the major diseases threatening the lives of the world, and the number of people suffering from cancer is increasing year by year. It is estimated based on the cancer model that: there will be 1,762,450 new cancer cases in the United States in 2019 (1,735,350 cases in 2018), and an average of 4,800 people will be diagnosed with cancer every day. Therefore, the cancer treatment has become an important problem in the current life science and medical field. Scientists have unendingly put forward treatment strategies for the treatment of cancer, such as photothermal therapy, photodynamic therapy, radiotherapy, chemotherapy, immunotherapy, and gene therapy. The photothermal therapy, photodynamic therapy, radiotherapy, and chemotherapy are often injected into the body by means of nanomaterials, to achieve the purpose of inhibiting and eliminating the tumor growth by using the EPR effect of the tumor tissue (i.e., the enhanced permeability and retention effect of solid tumor) and then with the help of a series of environments or substances adverse to tumor growth produced by light, heat, radiation, and chemical reactions. However, there are many problems in the current treatment schemes: the toxic and side effects on the liver caused by the long-term accumulation of nanomaterials in the body, the degradation and elimination from the body, and the targeting efficiency of the treatment method make it difficult to quickly apply these methods to the clinic.

With the continuously deepening of scientists' understandings on the cancer, in recent years, methods of immunotherapy and gene therapy have been proposed to be used in the tumor treatment. The immunotherapy is mainly a method of killing cancer cells and tumor tissues by activating the human immune system and relying on autoimmune functions. This treatment method differs from the previous treatment methods in that the target of immunotherapy is the body's own immune system rather than tumor cells and tissues, but the body's own immune system. The gene therapy refers to the introduction of exogenous normal genes into target cells to correct or compensate diseases caused by defect and abnormal genes to achieve the purpose of treatment. Although the gene therapy and immunotherapy can solve the problem of material metabolism, they have high technical requirements and relatively high costs, and it is difficult to popularize and implement them in the general public. How to develop effective anti-cancer therapies that meet the needs of the public has become an urgent problem in the current medical field.

As an endogenous gas, hydrogen gas has a relatively small molecular weight, is easy to diffuse, and has no toxicity and other side effects. It has attracted people's attention in the medical field, such as the treatment of Parkinson's disease, inflammation, rheumatic arthritis, liver cirrhosis, and acute skin erythema, but the cancer treatment by hydrogen gas is faced with major challenges. Hydrogen medicine first began in 1975. US scholars put the mice with skin squamous carcinoma in a hyperbaric chamber, and pressurized the animals with a mixed gas of hydrogen and oxygen to 8 atmospheres, wherein 98% of this gas is hydrogen. The animals lived in such an environment for 14 days, and the results showed that the tumors in many animals became smaller or even disappeared. However, there were relatively fewer reports of hydrogen in the cancer treatment afterwards, because the input of external hydrogen often relies on nanomaterials and such high-pressure devices. The problems of material metabolism and device limit the clinical use of hydrogen gas.

Acupuncture is to pierce a needle (usually a filiform needle) into the patient's body at a certain angle under the guidance of Chinese medicine theory, and use acupuncture manipulations such as twirling and lifting-thrusting to stimulate specific parts of the human body to achieve the purpose of treating diseases. As an important technique for the treatment of disease in Chinese medicine, it has been widely popularized and applied in the treatment of various diseases such as lumbar disc herniation, rheumatic arthritis, and nerve repair. How to establish a relationship between the acupuncture technology and cancer treat is a major challenge currently faced by Chinese medicine.

SUMMARY

The purpose of the invention is to adopt the principle of electrochemistry to combine the acupuncture technology with the electrochemical technology, and to adopt the principle of acidic tumor tissue to achieve the production of hydrogen gas in vivo through the electrolysis process of the acupuncture needle. The normal tissue produces a smaller amount of hydrogen gas, while the tumor tissue produces a larger amount of hydrogen gas, thus enabling the targeted localization and targeted burst of tumor tissue to produce therapeutic effects.

Thus, the invention provides the following items:
1. An electrochemical device for treating cancer, characterized by using an acupuncture needle as a working electrode to produce hydrogen in a tumor tissue, thereby destroying the tumor tissue through the produced hydrogen gas.
2. The electrochemical device according to above Item 1, wherein the acupuncture needle is used as an anode electrode, and/or the acupuncture needle is used as a cathode electrode.
3. The electrochemical device according to above Item 1 or 2, wherein the acupuncture needle is made of metal, and the metal has a stronger electrode activity than $H^+$ so as to produce hydrogen in the electrolysis reaction, and is preferably selected from magnesium, aluminum, and iron, most preferably iron.
4. The electrochemical device according to any one of above Items 1-3, wherein the tumor is a solid tumor, preferably selected from glioma, breast cancer, lymphoma, kidney tumor, neuroblastoma, germinoma, osteosarcoma, liver cancer, lung cancer, nasopharyngeal cancer, thyroid cancer, pancreatic cancer, colorectal cancer, and hemangioma.
5. A method for treating cancer by using the electrochemical device according to any one of above Items 1 to 4, including: (a) inserting the acupuncture needle as an electrode into a target tumor tissue; and (b) applying a voltage to the electrochemical device such that the cathode produces hydrogen, thereby performing the treatment.
6. The method according to above Item 5, wherein due to the acidic microenvironment of the tumor tissue, hydrogen gas accumulates in the tumor tissue to burst/destroy the tumor tissue, preferably inserting the electrode for producing $H_2$ gas into the center of the tumor tissue while placing the anode acupuncture needle close to the marginal area of the tumor.
7. The method according to above Item 5 or 6, wherein the exposed portions of the electrode are wrapped with an insulating material.
8. The method according to any one of above Items 5-7, wherein the treatment intensity is controlled by controlling the voltage applied to the electrochemical device and the application duration.
9. The method according to Item 8, wherein the applied voltage is 1-5 V, most preferably the applied voltage is 3 V, and the application duration is 10 min, and the treatment is performed twice a day for 3 consecutive days.
10. The method according to any one of above Items 5-9, wherein the acupuncture needle is a filiform needle, preferably with a diameter of 0.1-2 mm, preferably 0.2-1 mm, more preferably 0.3-0.5 mm, most preferably 0.35 mm, and the length is 10-200 mm, preferably 20-100 mm, more preferably 20-50 mm, most preferably 40 mm.

In another aspect, the invention also relates to use of the electrochemical device according to any one of the above Items 1-4 in the manufacture of a medical instrument for the treatment of cancer.

The invention adopts the acupuncture technology for the targeted localization of the tumor site (with little damage), subsequently in combination with the electrochemical hydrogen production technology to selectively burst tumor cells by means of the acidic microenvironment of tumor cells, thereby producing therapeutic effects. In addition, the method according to the invention produces enough hydrogen gas in the tumor tissue, and the hydrogen gas with a small molecular weight easily diffuses. A sufficient amount of hydrogen gas easily diffuses throughout the tumor tissue, while the proliferation of tumor cells at least takes several hours or sometimes even more than 20 hours. In this environment of hydrogen gas, the blood oxygen is reduced, the cell proliferation (diffusion) is difficult, while the residence time of hydrogen gas in vivo is also relatively long. Thus, the proliferation of tumor cells is difficult. After repeated treatments, all the tumor cells are essentially apoptotic, so it is difficult for the tumor cells to spread to other places throughout the treatment process. As to a tumor with a larger volume, a multi-needle treatment can be used to quickly eliminate the tumor.

Compared with other cancer therapies, the electrochemical hydrogen gas therapy ($H_2$-ECT) according to the invention has more benefits, including but not limited to:
1) low cost: the cost for the entire treatment process is no more than 1 dollar, solving the problem of the huge expenditure of cancer treatment unbearable for many families, and having a wide range of application prospects;
2) simple operations: complex biological modifications and chemical syntheses such as complicated material syntheses, drug syntheses, gene modifications, and antibody modifications are not needed, which is beneficial to saving manpower and time cost;
3) minimally invasive treatment: the damage of the treatment to tissues is reduced, which is beneficial to the repair and healing of normal tissues;
4) greenness and environmental friendliness: the hydrogen gas takes the place of the toxic gas treatment strategy, and for the first time achieves the cancer treatment by Chinese medicine combined with the electrochemical in vivo hydrogen production, to avoid the metabolic problem of nanomaterial in the process of tumor treatment and the toxic effect to the liver by nanomaterial accumulation;
5) relatively simple and cheap equipment: no expensive equipment is needed, and the treatment on the internal tumor in the later stage can be assisted by using medical image for precise treatment.

DESCRIPTION OF EMBODIMENTS

The technical solutions of the invention will be described in more detail below in conjunction with the accompanying drawings.

Figure 1:
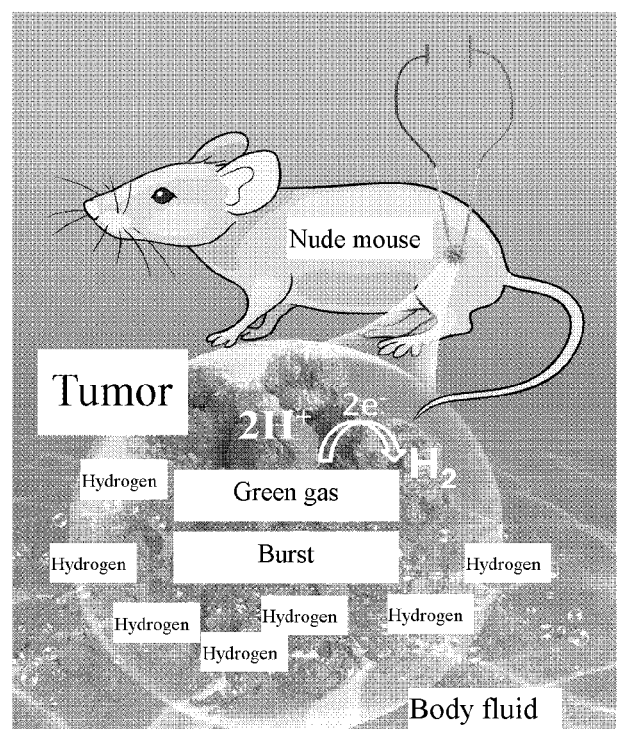
FIG. 1 The acupuncture combined with the electrochemical in vivo hydrogen production method is used for cancer treatment.

The overall technical scheme of the invention is shown in FIG. 1.

1) In Vitro Electrochemical Hydrogen Production

The cell microenvironments of normal cells and cancer cells have important differences, and especially the pH of normal cells and cancer cells has obvious differences. Therefore, the hydrogen production situations under the simulated body fluids (SBF, designed using ion concentrations in human plasma as templates, mainly containing sodium ion, potassium ion, chloride ion, magnesium ion, carbonate ion, phosphate ion, sulfate ion, etc., commercially available) at different pH values were first verified. The simulated body fluids at different pH values (pH=5.5, 6.0, 6.5, 7.0, and 7.5, respectively) were first adjusted, then a three-electrode system (working electrode: acupuncture electrode (filiform needle, 0.35 mm in diameter and 40 mm in length); counter electrode: acupuncture electrode (filiform needle, 0.35 mm in diameter and 40 mm in length); reference electrode: Ag/AgCl) was used to determine the polarization curves under different pH and voltages. The polarization curve mainly adopted the negative scanning method, with a scanning range of from 0 V to −3V, and the hydrogen production rates at different pH were observed by the polarization curve. Then, the products in the electrolysis process were identified. The inventors speculated that the cathode and anode products and the reaction were as follows respectively:

Cathode reaction(cathode): $2H^+ + 2e^- \rightarrow H_2$;

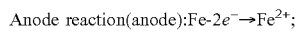

Figure 2:
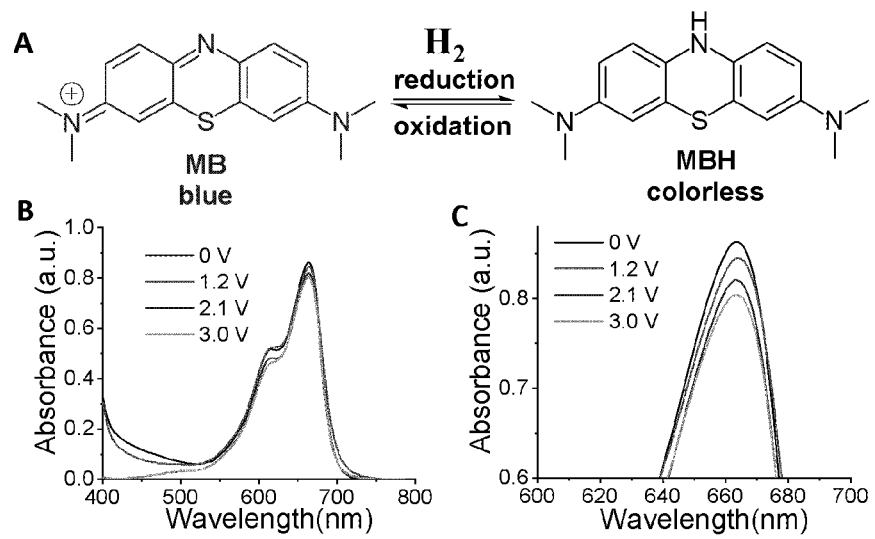
FIG. 2 (A) shows the mechanism of reduction of methylene blue by hydrogen gas; (B) and (C) show the change of UV absorption after the action of simulated body fluid (pH=6.0) with methylene blue under different voltage stimulations (from top to bottom: 0 V, 1.2 V, 2.1V, 3.0 V)

Anode reaction(anode): $Fe - 2e^- \rightarrow Fe^{2+}$;

In order to prove that the gas produced by the cathode is hydrogen gas, the methylene blue reduction method was used, and the reaction mechanism is shown in FIG. 2.

The inventors observed that for the absorption of methylene blue, the UV absorption gradually decreased with the increase of voltage, indicating that with the increase of voltage, the amount of the produced hydrogen gas increased, demonstrating that the hydrogen gas was produced by the cathode during this electrolysis process.

The inductively coupled plasma spectrometer (ICP-OES) (Thermo Scientific iCAP Type 6300, U.S.A) and X-ray photoelectron spectroscopy (XPS) (VG Scientific ESCALAB MKII spectrometer, U.S.A.) were used in the anode product analysis. First, by ICP-MS, the inventors determined the iron consumption on the working electrode at different times (0, 5, 10, 15, 20 min), different voltages (0, 1.2, 2.1, and 3.0 V), and different pH (5.5, 6.0, 6.5, 7.0, and 7.5) by the control variable method. The volume of hydrogen gas produced on the cathode electrode was calculated through the iron consumption.

Figure 3:
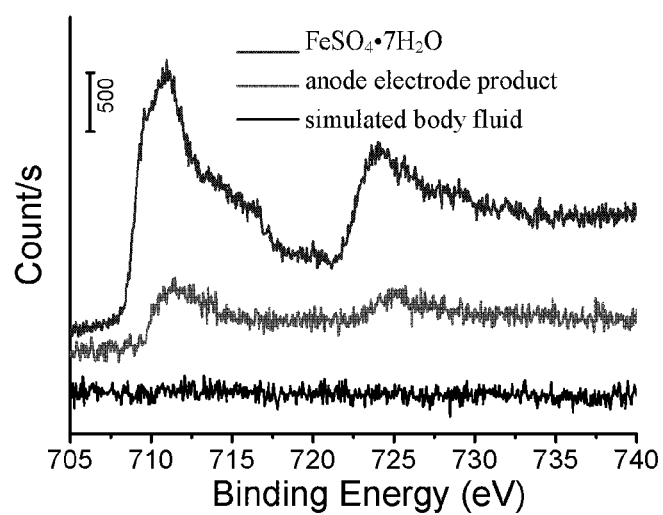
FIG. 3 XPS spectra of simulated body fluid (SBF), anode electrode product, and $FeSO_4.7H_2O$ standard sample (from top to bottom, respectively: $FeSO_4.7H_2O$, anode electrode product, and SBF)

In order to prove that the iron ions produced by the anode are divalent iron ions, the inventors used XPS to determine the energy spectrum of the product, and $FeSO_4 \cdot 7H_2O$ was selected as the control sample. The energy spectrum of the anode product was consistent with the energy spectrum position of the control sample. The results demonstrate that the generated anode product is divalent iron (see FIG. 3).

2) Toxicity of Produced Iron Ions

Figure 4:
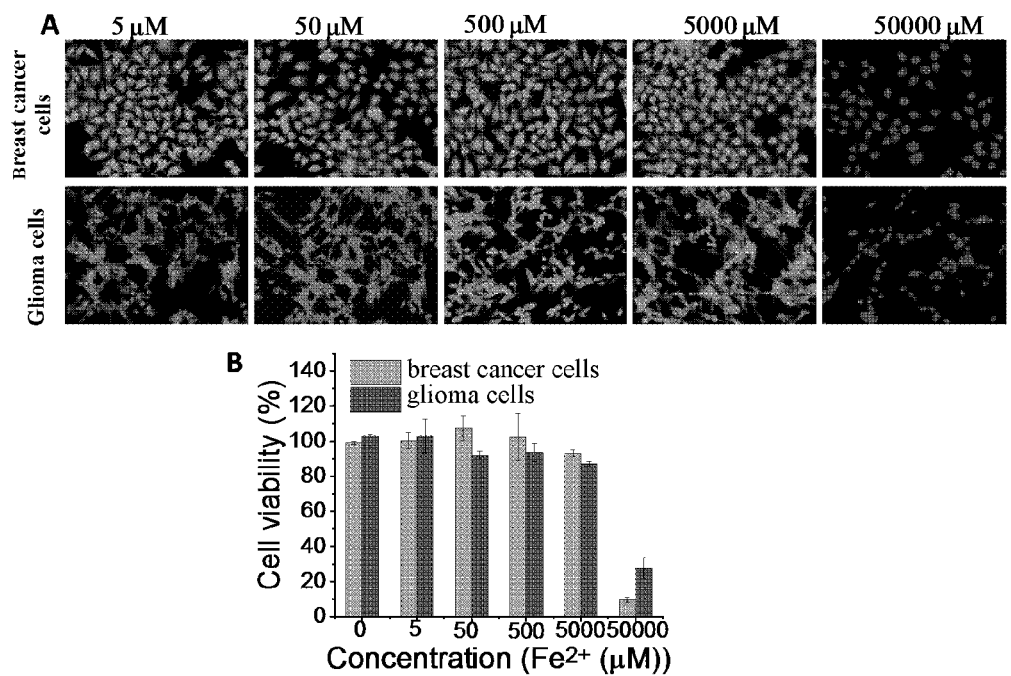
FIG. 4 Verification of the toxicities of different concentrations of iron ions to cells.

To study the toxicity of the anode product $Fe^{2+}$ during the electrochemical hydrogen therapy ($H_2$-ECT), the inventors selected MCF-7 (breast cancer cells) (American Type Culture Collection) and C6 (rat glioma cells) (American Type Culture Collection) as research models, and utilized the standard MTT kit (Shanghai Aladdin Biochemical Technology Co., Ltd.) and live cell and dead cell fluorescent dye (calcein/pyridine iodide (AM/PI)) (Sigma-Aldrich Trading Co., Ltd.), to study the toxicities of different concentrations of $Fe^{2+}$ (0.139 g of $FeSO_4 \cdot 7H_2O$ were weighed and dissolved in 10 mL of DMEM complete medium to obtain 50 mM of $Fe^{2+}$ concentration, the concentration of $Fe^{2+}$ was then diluted using the complete medium to obtain the required $Fe^{2+}$ concentration) to cells. The experiment results are shown in FIG. 4. From fluorescence imaging and MTT experiment, it can be seen that when the iron ion concentration is lower than 5 mM, the iron ion has no effect on cell activity. Since the electrolysis was conducted by the inventors at pH=6.0 for 10 min, the produced $Fe^{2+}$ via the electrogravimetric analysis is 2.5 μM, and thus the cytotoxicity of $Fe^{2+}$ produced by the anode can be ignored in this research. It is $H_2$ that mainly plays a leading role in this research.

Figure 5:
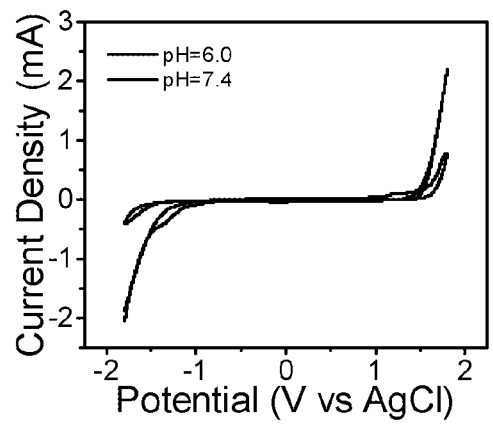
FIG. 5 Cyclic voltammetry curves of fresh pork tissues with different pH values (from top to bottom, respectively: pH=6.0; pH=7.4)
Figure 6:
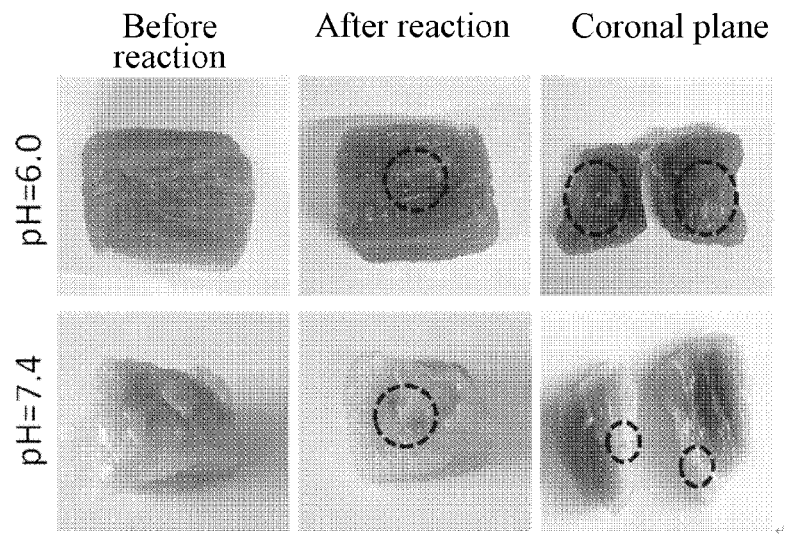
FIG. 6 Pictures before and after $H_2$-ECT treatment for fresh pork tissues after soaked in simulated body fluids (SBF) with different pH values (6.0 and 7.4) for 24 hours.

3) Electrochemical Hydrogen Production and Damage Verification on the Tissue Level The inventors used the fresh pork tenderloin tissue and soaked the pork tissue in SBF solutions at pH=6.0 and pH=7.4 for 24 h. Then the aforementioned three electrodes were inserted into the tissue respectively for the polarization curve and cyclic voltammetry curve (CV) scanning (the experiment results are shown in FIG. 5). Similarly, the acidic tissue is more conducive to the production of hydrogen gas, further demonstrating that the inventors' envisagement is reasonable. The inventors cut the tissue along the coronal plane to observe the degree of tissue damage (the experiment results are shown in FIG. 6). It can be clearly seen that, in the acidic tissue, the hydrogen electrochemical treatment ($H_2$-ECT) exhibited more serious damage to the tissue, while the damage degree in the neutral tissue was relatively small. It is also fully shown that $H_2$-ECT has good selectivity for the tumor tissue.

4) Verification of Hydrogen Gas Production at the Tumor In Vivo

In order to prove that this method can produce hydrogen gas in the tumor tissue, the inventors first established a tumor model of C6 cells. First, the cells were inoculated into healthy nude mice by the cell transplantation method (approximately 4 weeks), and the mice were observed for two weeks until tumor formation. Then the in vivo gas production in mice was verified by the $H_2$-ECT method.

Figure 7:
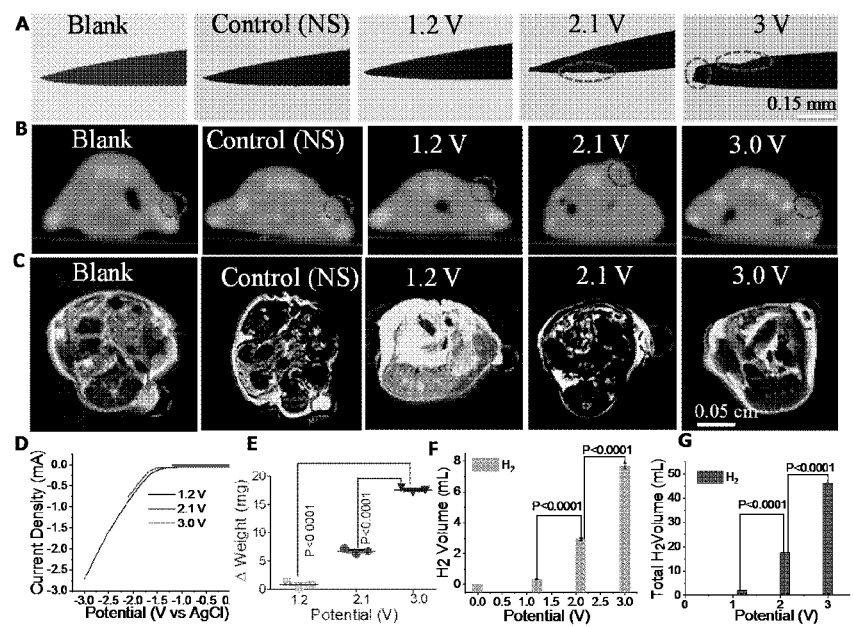
FIG. 7 (A) shows the microscopic pictures after $H_2$-ECT by inserting the anode acupuncture electrode needle into the tumor tissue under different voltages (0, 1.2, 2.1, and 3.0 V). (B) and (C) show in vivo CT and NMR gas imaging in different control groups of cancer-bearing mice. (D) shows the polarization curves under different voltage within the tumor. (E) shows the anode electrode consumption changes measured by electrogravimetric method after in vivo $H_2$-ECT (10 min) under different voltages. (F) shows the volume changes of hydrogen gas produced at the tumor site after one treatment with different voltages. (G) shows the volume changes of total hydrogen gas produced under different voltages (0, 1.2, 2.1, and 3.0 V) throughout the treatment process.

First, the inventors intraperitoneally injected 10 wt % chloral hydrate into the tumor-bearing mice, such that the mice were under general anesthesia. Then the sterilized portions of two stainless sterile acupuncture needles were inserted into the tumor tissue, while the portions not inserted into the tumor tissue were insulated by the plastic rubber tube, to prevent the occurrence of short circuit at the same time. Different voltages were applied, and the treatment time was 10 min. Under the microscope, the inventors found that the anode electrode needle was consumed. When the voltage was 1.2 V, the consumption of acupuncture electrode increased as the voltage increased (as shown in FIG. 7A). In order to further prove that the tumor site was accompanied with the gas production during the electrochemical treatment, the inventors used both nuclear magnetic imaging and CT imaging for verification. It can be clearly seen from FIGS. 7B and 7C that: with the increase of the voltage, the cavity at the tumor site gradually becomes larger, which is sufficient to prove the gas production during this treatment process.

The polarization curve of the $H_2$-ECT tumor site was essentially consistent with the in vitro test (FIG. 7D). With the increase of voltage, the mass of the consumed anode electrode increased, and the volume of produced hydrogen gas increased. According to the electrogravimetric analysis and Faraday's law, the inventors calculated that the hydrogen gas produced at the tumor site in a single treatment was approximately 7.69 mL (FIGS. 7E and 7F). Throughout the electrochemical treatment process, the inventors conducted the treatment twice a day for three consecutive days. The final volume of hydrogen gas produced throughout the process was 46.1 mL (FIG. 7G).

5) The tumor treatment was evaluated using the evaluation system.

6) The safety of $H_2$-ECT was evaluated using immunohistochemistry as well as blood routine and trace elements.

Example 1

1) Establishment of C6 Tumor Model

Glioma, as one of the malignant tumors, is difficult to be clinically cured at present. The inventors used the $H_2$-ECT method for the treatment of this tumor.

Firstly, the inventors cultured C6 glioma cells under the following culture conditions: DMEM medium, 10% fetal bovine serum, 100 U/mL penicillin, 100 μg/mL streptomycin, at 37° C. and 5% $CO_2$. The cells were collected, such that the number of cells injected into each mouse (BALB/c nude mice, Beijing Huafukang Biotechnology Co., Ltd.) (four-week old) was 1 million. The tumor cells were subcutaneously transplanted into the mice, and then the transplanted mice were observed. After the tumor was formed in mice (6 weeks), the volume change of the tumor was observed. When the volume of the tumor was 200 cm³, the $H_2$-ECT treatment was initiated.

Firstly, the cancer-bearing mice were grouped: the control group was divided into two groups, one involving no treatment at all, and the other only involving acupuncture stimulation without applying electricity. The experiment group were subjected to the $H_2$-ECT treatment regimens under different voltages at the stimulation time of 10 min. The tumor-bearing mice were treated and observed for half a month, wherein the mice were treated twice a day for the first three days, and observed for recovery in the later twelve days. The daily body weights were recorded, and the tumor volume changes were recorded and photographed.

Figure 8:
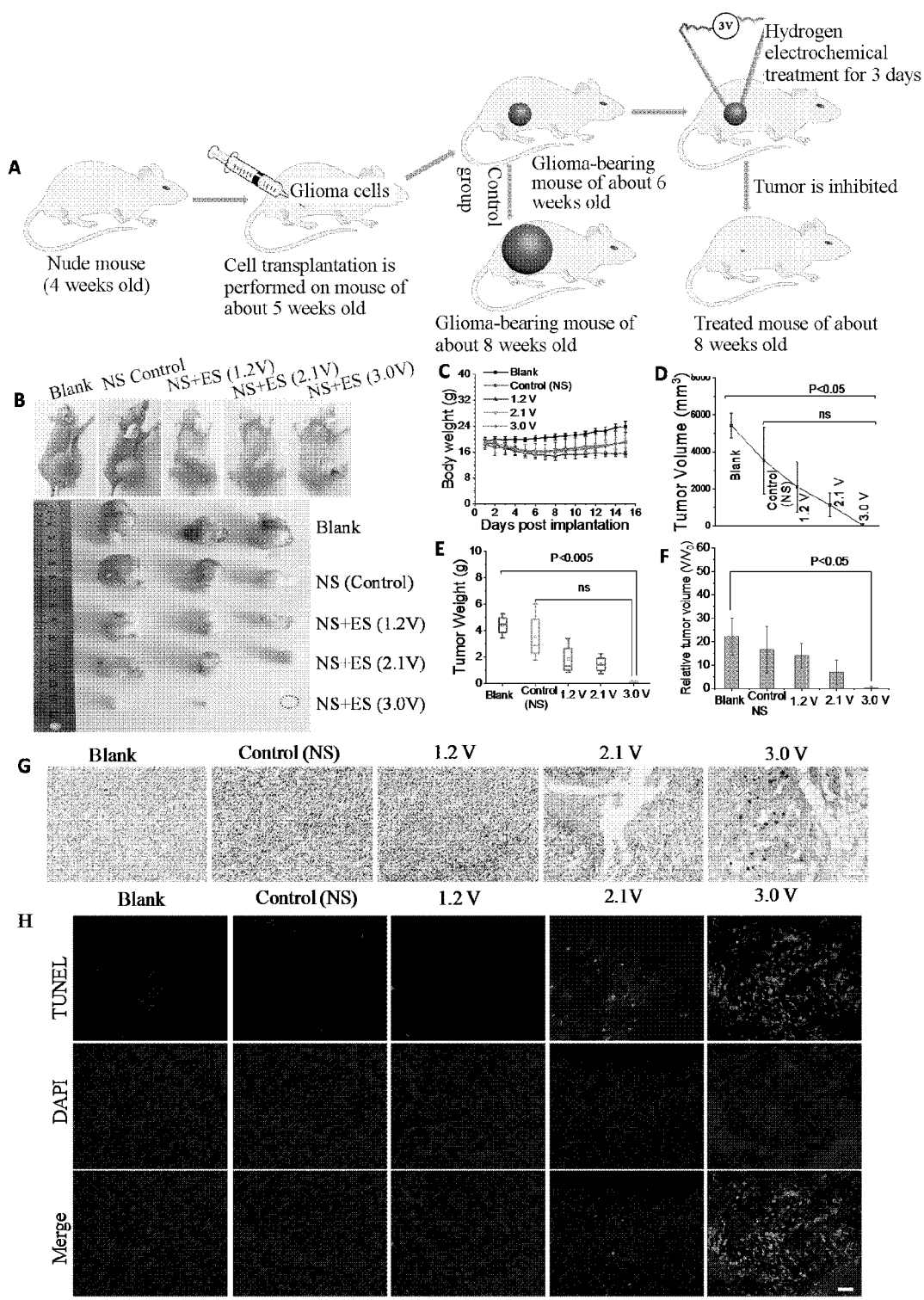
FIG. 8 A shows the flowchart of cancer cell transplantation in mice as well as tumor formation and treatment. B shows the pictures of the body type and tumor size of the cancer-bearing mice after different treatment regimens. C shows the daily body weight change of mice in half a month. D-F show the tumor volume, tumor mass, and relative tumor volume of cancer-bearing mice in the experiment and control groups. G shows HE staining of tumor tissues after different treatments. H shows TUNEL (terminal deoxynucleotidyl transferase) fluorescence imaging of different tumor tissues after treatment.

2) Evaluation of $H_2$-ECT Treatment Results a) Firstly, the inventors took photographs and observations and tumor dissection experiments on the treated mice on the 16th day. The inventors found that the tumors of the mice decreased with the increase of voltage. When the voltage was 3.0 V, the tumor was essentially disappeared. Throughout the treatment process, the inventors found that the body weights of the mice essentially remained unchanged, which also illustrates the safety of this method (FIG. 8C). The inventors weighed the dissected tumor tissues of different control groups, measured the volumes, and calculated the relative volumes. The results showed that with the increase of voltage, the volume, mass, and relative tumor volume of the tumor decreased (FIG. 8D-F).

b) Immunohistochemical Analysis (HE Staining)

The inventors carried out the immunohistochemical analysis on the tumor tissues in the experiment and control groups in the treatment process. First, the mice were executed by dislocation, and the tumor tissues were taken out by anatomy and then the tissues were fixed with 4% paraformaldehyde. The hematoxylin-eosin staining (HE) was finally conducted, and the changes of the tumor cells before and after treatment were observed under the microscope. As shown in FIG. 8G, when the tumor tissue cells were under a voltage of no less than 2.1 V, the damage of tumor cell membrane as well as the shrinkage and deletion of the cell nucleus occurred, while the tumor cells in other low-voltage and control groups maintained their integrities. Thus, the results showed that the $H_2$-ECT has a good therapeutic effect.

c) TUNEL Fluorescence Imaging Analysis

At the same time, the inventors studied the effect of this treatment on DNA on the molecular level. First, the inventors used the TUNEL kit (Thermo Fisher Scientific Co., Ltd.) to stain the tumor tissue. The cell nucleus was stained with 1 μM DAPI. The TUNEL staining principle is as follows: the fluorescein labeled 12-dUTP is attached to the 3'-OH end of broken DNA in the apoptotic cell under the action of terminal deoxynucleotidyl transferase (TdT), and the occurrence of apoptosis was detected using a fluorescent microscope or flow cytometer by fluorescence imaging analysis. As shown in FIG. 8H, the inventors found that the DNA breakage degree of the cell nucleus within the tumor cell was significantly increased with the increase of voltage. On the molecular level, these results showed that the $H_2$-ECT treatment can promote the DNA breakage in cancer cells, thereby inducing apoptosis.

d) $H_2$-ECT Safety Evaluation of Other Organs in Mice Suffered from Glioma

Figure 9:
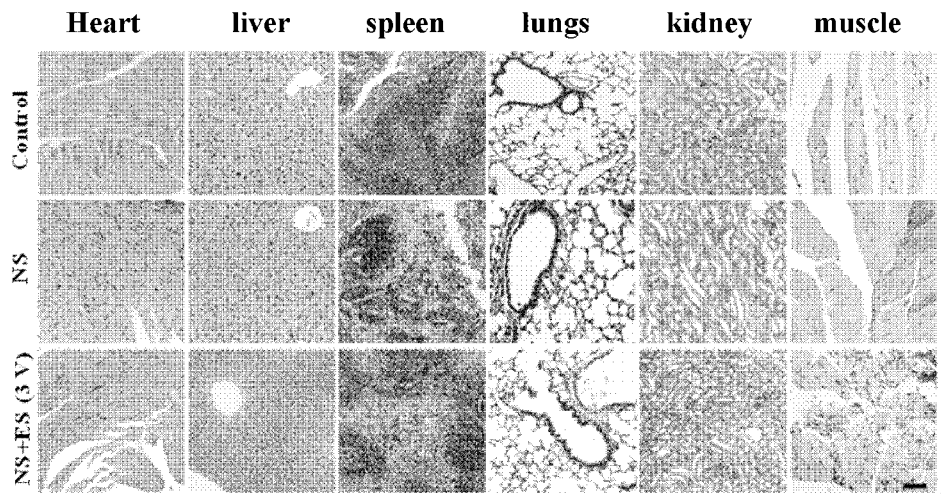
FIG. 9 HE staining microscopic pictures of various organs of mice in the experiment and control groups.

First, all the mice in the control and experiment groups (three mice were used in the parallel experiment in each group) were dissected, and each of organs was collected for immunohistochemical analysis. The main organs included muscles near the tumor, heart, liver, spleen, lung, and kidney. As shown in FIG. 9, obvious staining of cell cytoplasm and nucleus can be seen in the HE staining of each organ, and apart from pulmonary cells, the cells in other organs were tightly arranged. These sufficiently showed that the $H_2$-ECT treatment method does not affect every organ in the body, which further illustrates the safety of this method.

e) $H_2$-ECT Safety Evaluation of Blood Routine in C6 Model Mice

Figure 10:
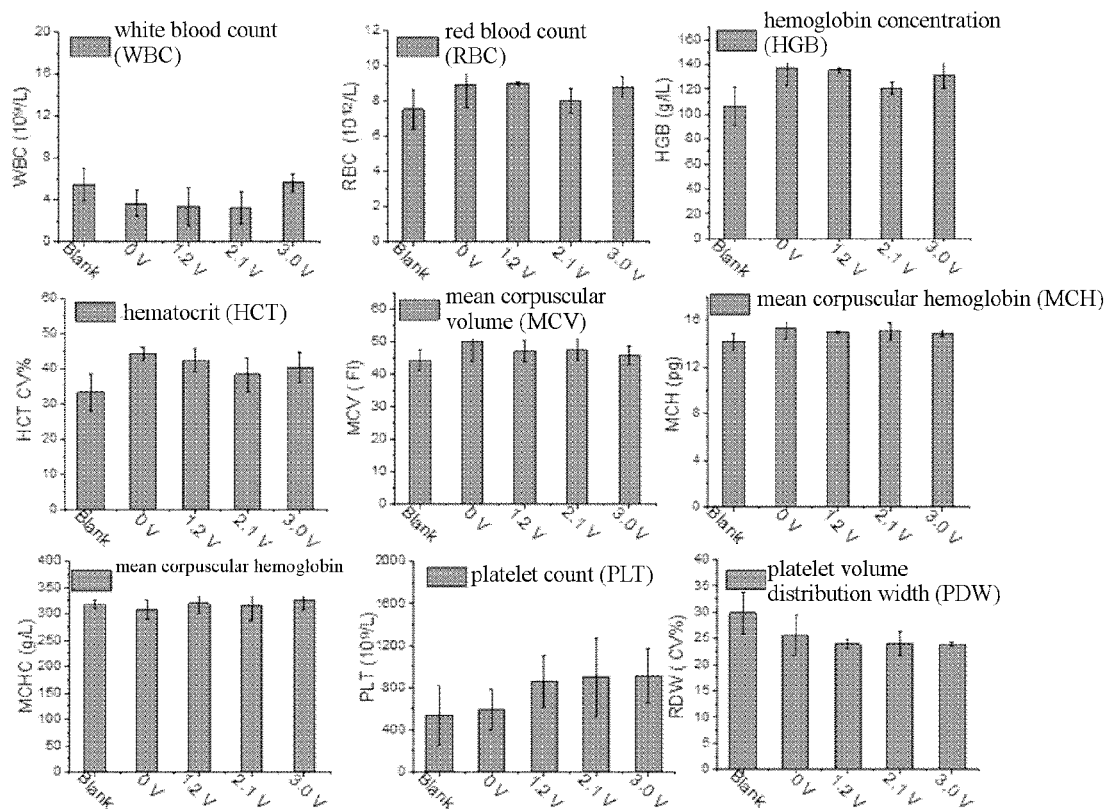
FIG. 10 Routine blood determinations of healthy, control, and experiment groups (1.2, 2.1, and 3.0 V)

The mice were divided into healthy, control, and experiment groups, and three mice were used in the parallel experiment in each group. After the treatment and recovery period for half a month, the mice were subjected to eyeball blood drawing to collect a certain number of blood in the anticoagulant tube, which was then grouped and labeled for blood routine determination. The blood routine determination mainly included: white blood count (WBC), red blood count (RBC), hemoglobin concentration (HGB), hematocrit (HCT), mean corpuscular volume (MCV), mean corpuscular hemoglobin (MCH), mean corpuscular hemoglobin concentration (MCHC), platelet count (PLT), and platelet volume distribution width (PDW). By comparing healthy mice with each experiment and control group, the inventors found that each blood routine index essentially had a little change (as shown in FIG. 10).

f) Trace Element Analysis of $H_2$-ECT in C6 Cancer Model Mice

Figure 11:
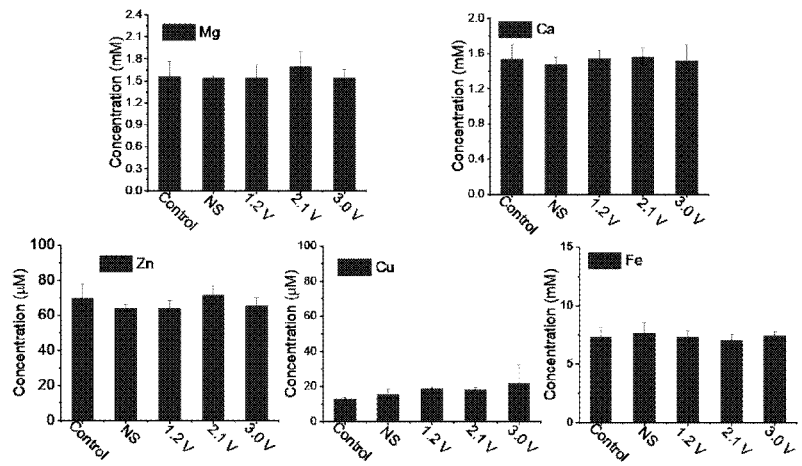
FIG. 11 Changes of trace elements in the blood of mice in the experiment and control groups.
Figure 12:
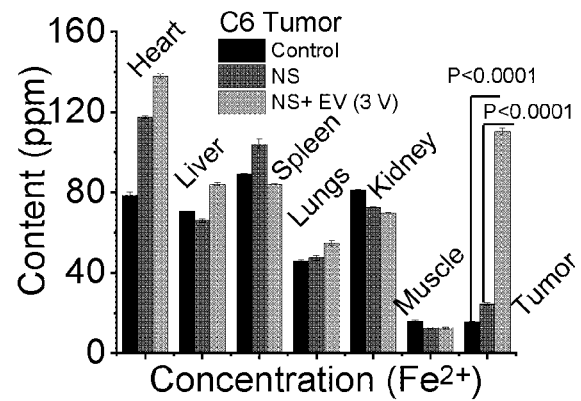
FIG. 12 Distributions of iron element in each organ and tumor site in the control and experiment groups (for the data of each organ, from left to right, respectively: control, NS, and NS+EV (3V))

The inventors also collected blood from eyeballs in the treated, untreated, and healthy mice, and then determined the trace element changes in the blood components in each group. The trace elements to be mainly determined included Fe, Cu, Mg, Zn, and Ca. By comparing the experiment results, the inventors found that the $H_2$-ECT treatment method substantially had no interference on the trace elements in the blood (FIG. 11). Thus, this method was proven to have reliable safety applications.

g) In Vivo Distribution of $H_2$-ECT Anode $Fe^{2+}$ in Each Organ of C6 Model Mice In order to prove that this method does not have the problem of difficult metabolism, the inventors carried out the iron element determination for the iron ion produced by the anode in each organ. First, each organ (heart, liver, spleen, lung, kidney, and muscles near the tumor) was obtained by anatomy, then weighted and dissolved with aqua regia, and finally detected by the inductively coupled plasma spectrometer (Thermo Scientific iCAP Type 6300, U.S.A.). The inventors found that in this $H_2$-ECT treatment method, $Fe^{2+}$ produced by the anode mainly accumulated at the tumor site, and there was no significant abnormality in other organs (FIG. 12). At the same time, it was demonstrated that this methods does not have the problem of difficult metabolism. This method solved the major problem of clinical use difficulties encountered by current nanomaterials, and thus this method has potential clinical use values.

Example 2

1) Establishment of MCF-7 Breast Cancer Model

First, MCF-7 cells were cultured. The culture conditions for MCF-7 cells were as follows: DMEM medium, 10% fetal bovine serum, 100 U/mL penicillin, 100 µg/mL streptomycin, at 37° C. and 5% $CO_2$, sterile culture. Then 0.25 wt % trypsin was used for digestion to obtain suspended cells. A certain number of cells were collected and centrifuged (rotation speed: 1000 r/min, 5 min), washed with PBS (10 mM, pH=7.4), and then centrifuged to remove cells debris, to obtain a clean monodispersed cell suspension. The cells were counted by a cell counting plate, to ensure that the number of cells injected into each mouse was approximately 1 million. MCF-7 cells were transplanted by subcutaneous injection into the mice. Then the tumor formation was monitored. When the volume of the tumor was about 200 $cm^2$, the $H_2$-ECT treatment was conducted.

2) In Vivo Treatment of MCF-7 Breast Cancer

First, the models were grouped, wherein each group included three parallel experiments. Then each of grouped mice was anaesthetized by intraperitoneally injecting 10 wt % chloral hydrate. When all the mice were under anesthesia, the alcohol cotton soaked with 75 wt % alcohol was used to sterilize the tumor site, and the sterile acupuncture needle was installed with a plastic casing for insulating treatment, with an insertion depth into the tumor of about 5 mm. As to the insertion positions of two acupuncture electrodes, the cathode producing $H_2$ gas was tried to insert into the central portion of the tumor tissue, while the anode acupuncture needle can be close to the marginal area of the tumor. This operation prevented the gas produced at the edge from spreading to normal tissues. When two acupuncture electrodes were inserted into the tumor region, the constant power source was turned on, such that the voltage was at 3.0 V, and the recorded treatment time was 10 min. At 10 min, the power source was turned off, and two acupuncture electrodes were gently pulled out. The inserted portions of the electrodes were disinfected to avoid bacterial infection. In the same manner, each of cancer-bearing mice was treated twice a day for three consecutive days, and observed for recovery in the later twelve days. The body weights of mice were recorded daily, and the tumor volume changes of mice were measured daily.

3) Determination of the Therapeutic Effect of $H_2$-ECT on MCF-7 Mouse Model

Figure 13:
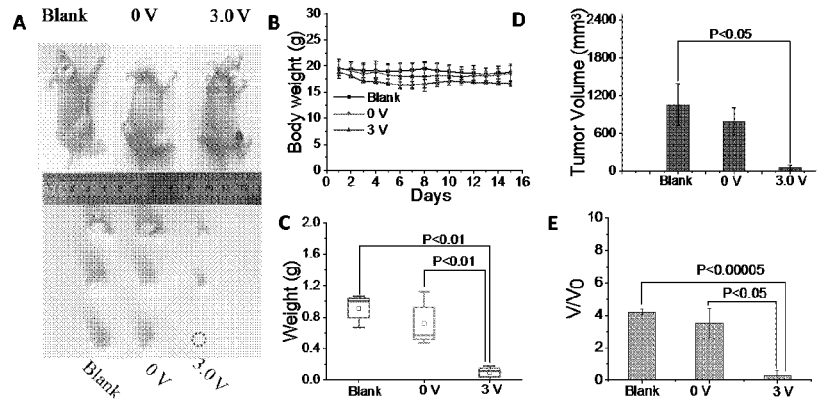
FIG. 13 A shows the pictures of tumor changes in mice after treatment. B shows the weight changes of mice during the treatment and recovery (from top to bottom, respectively: blank, 0 V, and 3 V). C-E show the changes of the tumor mass, volume, and relative tumor volume in the experiment and control groups after $H_2$-ECT treatment.

After the treatment and recovery period for half a month, it was observed that the mice suffered from MCF-7 tumor showed significantly smaller or even disappeared tumor after the treatment under a voltage of 3V for 10 min (FIG. 13A). At the same time, the inventors executed the mice in the experiment and control groups by dislocation to dissect and take out the tumor. By comparing the volume, weight, and relative tumor volume change of the tumor, the inventors found that the $H_2$-ECT treatment at 3 V for 10 min had a good therapeutic effect. The weights of mice essentially remained unchanged, which indirectly shows the reliability and safety of this method (FIG. 13B-E).

4) $H_2$-ECT Safety Evaluation in Other Organs

The inventors carried out the safety evaluation of this treatment method on each organ of other treated mice. First, the inventors dissected all the mice in the control and experiment groups, and collected each organ thereof for immunohistochemical analysis. The main organs included muscles near the tumor, heart, liver, spleen, lung, and kidney.

Figure 14:
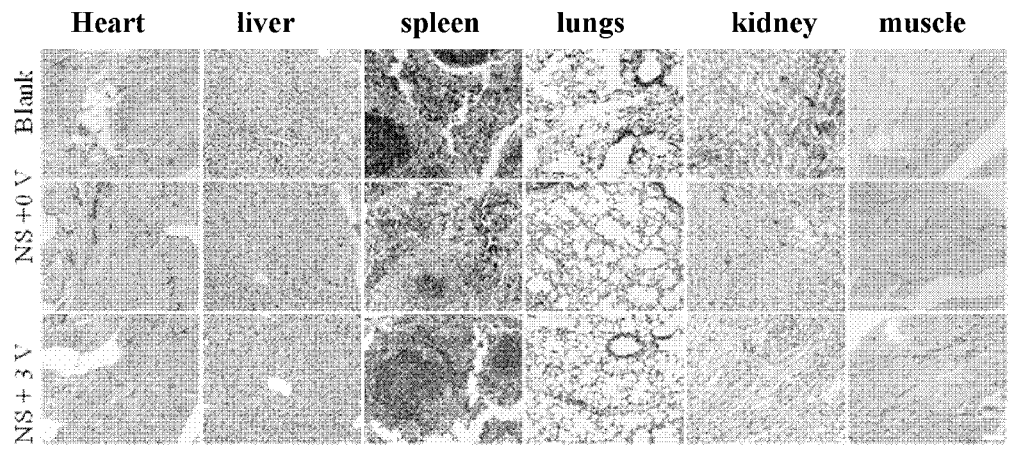
FIG. 14 HE staining of various organs in three groups (control and experiment groups)

As shown in FIG. 14, obvious staining of cell cytoplasm and nucleus can be seen in the HE staining of each organ, and apart from pulmonary cells, the cells in other organs were tightly arranged. These sufficiently showed that the $H_2$-ECT treatment method does not affect every organ in the body, which further illustrates the safety of this method.

5) $H_2$-ECT Safety Evaluation of Blood Routine

Figure 15:
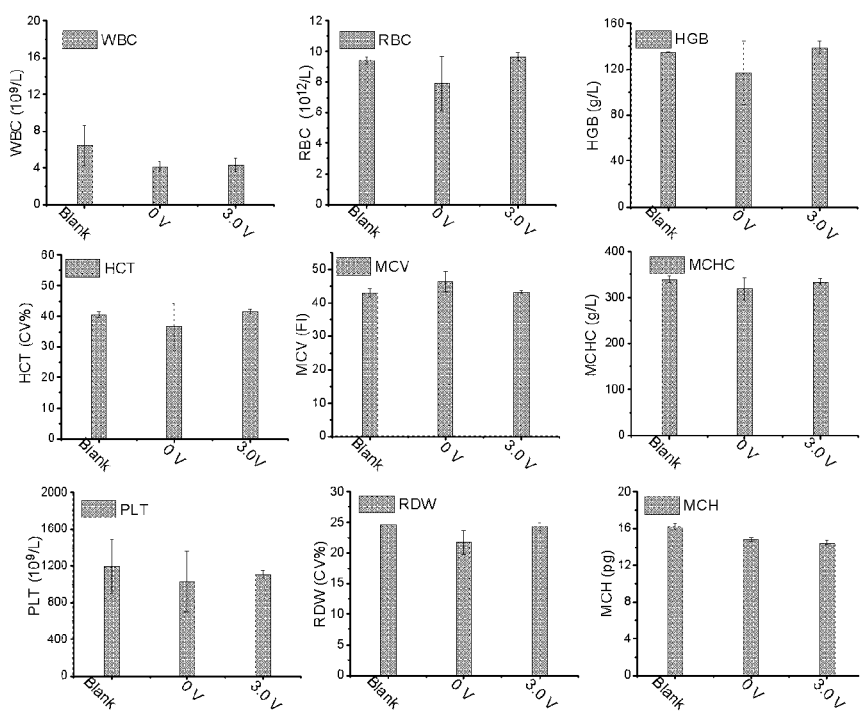
FIG. 15 Routine blood determination of the control and experiment groups.

The inventors compared the blood of treated nude mice of MCF-7 model in the control and experiment groups with that of healthy mice, respectively. The inventors collected blood from mice via eyeball blood drawing, and then determined the blood routine for mice in the control and experiment groups and healthy mice. The results are shown in FIG. 15. It can be clearly seen that the blood routine indexes of treated mice were consistent with those of healthy mice, which also sufficiently illustrated that the $H_2$-ECT has no interference on the blood components.

6) Trace Element Analysis of $H_2$-ECT in MCF-7 Cancer Model Mice

Figure 16:
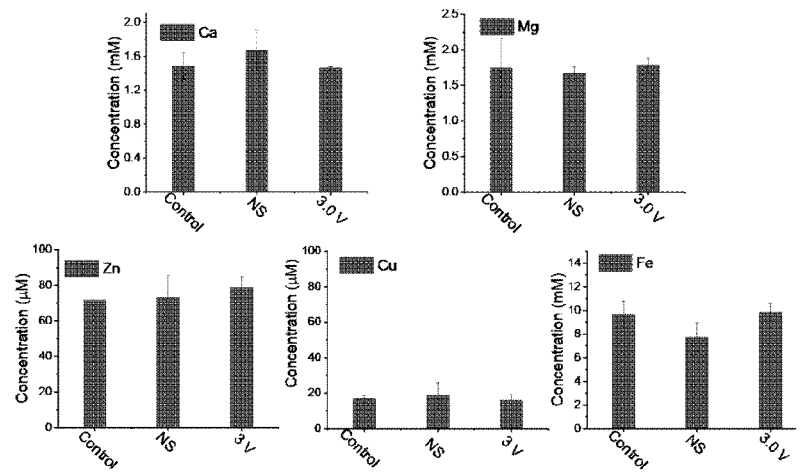
FIG. 16 Changes of trace elements in the blood of mice in the experiment and control groups.

In the process of $H_2$-ECT treatment, the inventors found that the anode was accompanied with $Fe^{2+}$ production. To show whether this will affect the changes of trace elements in the blood, the inventors also collected blood via eyeball blood drawing, and compared the trace elements of mice in the experiment and control groups with those in healthy mice. The results are shown in FIG. 16. It can be clearly seen that, during the treatment, the contents of trace elements Ca, Cu, Zn, Mg, and Fe essentially remained unchanged. This also illustrated that this method will not affect the changes of trace elements in vivo, which proves the safety of $H_2$-ECT.

Figure 17:
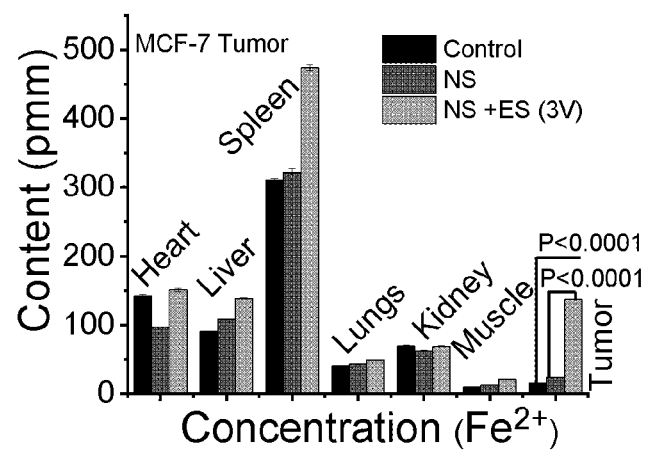
FIG. 17 Distributions of iron element in each organ and tumor site in the control and experiment groups (for the data of each organ, from left to right, respectively: control, NS, and NS+EV (3V)).

7) In Vivo Distribution of $H_2$-ECT Anode $Fe^{2+}$ in Each Organ of C6 Model Mice This in vivo electrochemical hydrogen treatment method produces $Fe^{2+}$ at the anode. The inventors detected the distribution of produced divalent iron ions using the inductively coupled plasma spectrometer (Thermo Scientific iCAP Type 6300, U.S.A.). First, each organ and tumor site in the control and experiment groups was weighted, and dissolved with aqua regia. Then the content change of Fe element in each organ was determined. The results are shown in FIG. 17. It was found that Fe ions mainly accumulated at the tumor site, and did not accumulate in other organs. This also sufficiently illustrates that this method can fully solve the problems of liver accumulation and metabolism difficulty encountered by nanomaterials and nanodrugs in clinic, which fully reflects the reliability of the $H_2$-ECT treatment method and broader clinical use prospects.

What is claimed is:

1. A method for treating cancer by using an electrochemical device comprising an acupuncture needle used as an anode electrode and an acupuncture needle used as a cathode electrode, the method comprising:
    inserting the acupuncture needle used as the cathode electrode into a center of a target tumor tissue;
    placing the acupuncture needle used as the anode electrode on a marginal area of the target tumor tissue; and
    applying a voltage to the electrochemical device such that the acupuncture needle used as the cathode electrode produces hydrogen gas in the target tumor tissue, thereby destroying the target tumor tissue through the produced hydrogen gas,
    wherein the acupuncture needle used as the cathode electrode is made of metal,
    wherein the metal has a stronger electrode activity than H+ so as to produce hydrogen in an electrolysis reaction and is selected from the group consisting of magnesium, aluminum, and iron.

2. The method according to claim 1, wherein due to an acidic microenvironment of the target tumor tissue, the produced hydrogen gas accumulates in the target tumor tissue to burst/destroy the tumor tissue.

3. The method according to claim 1, wherein exposed portions of at least one of the acupuncture needle used as the cathode electrode or the acupuncture needle used as the anode electrode are in a form wrapped with an insulating material.

4. The method according to claim 1, wherein a treatment intensity is controlled by controlling the voltage applied to the electrochemical device and an application duration.

5. The method according to claim 4, wherein the applied voltage is 1-5 V, the application duration is 10 min, and the treatment is performed twice a day for 3 consecutive days.

6. The method according to claim 4, wherein the applied voltage is 3 V, the application duration is 10 min, and the treatment is performed twice a day for 3 consecutive days.

7. The method according to claim 1, wherein at least one of the acupuncture needle used as the cathode electrode or the acupuncture needle used as the anode electrode is a filiform needle with a diameter of 0.1-2 mm and a length of 10-200 mm.

8. The method according to claim 1, wherein at least one of the acupuncture needle used as the cathode electrode or the acupuncture needle used as the anode electrode is a filiform needle with a diameter of 0.2-1 mm and a length of 10-200 mm.

9. The method according to claim 1, wherein at least one of the acupuncture needle used as the cathode electrode or the acupuncture needle used as the anode electrode is a filiform needle with a diameter of 0.3-0.5 mm and a length of 10-200 mm.

10. The method according to claim 1, wherein at least one of the acupuncture needle used as the cathode electrode or the acupuncture needle used as the anode electrode is a filiform needle with a diameter of 0.35 mm and a length of 10-200 mm.

11. The method according to claim 1, wherein at least one of the acupuncture needle used as the cathode electrode or the acupuncture needle used as the anode electrode is a filiform needle with a diameter of 0.1-2 mm and a length of 20-100 mm.

12. The method according to claim 1, wherein at least one of the acupuncture needle used as the cathode electrode or the acupuncture needle used as the anode electrode is a filiform needle with a diameter of 0.1-2 mm and a length of 20-50 mm.

13. The method according to claim 1, wherein at least one of the acupuncture needle used as the cathode electrode or the acupuncture needle used as the anode electrode is a filiform needle with a diameter of 0.1-2 mm and a length of 40 mm.

14. The method according to claim 1, wherein the target tumor tissue comprises a solid tumor selected from the group consisting of glioma, breast cancer, lymphoma, kidney tumor, neuroblastoma, germinoma, osteosarcoma, liver cancer, nasopharyngeal cancer, thyroid cancer, pancreatic cancer, colorectal cancer, and hemangioma.

* * * * *